United States Patent
Iwashita et al.

(10) Patent No.: US 11,430,161 B2
(45) Date of Patent: Aug. 30, 2022

(54) IMAGE PROCESSING APPARATUS, IMAGE PROCESSING METHOD, AND PROGRAM

(71) Applicant: CANON KABUSHIKI KAISHA, Tokyo (JP)

(72) Inventors: Atsushi Iwashita, Tokyo (JP); Akira Tsukuda, Kawasaki (JP); Kosuke Terui, Yokohama (JP); Sota Torii, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 212 days.

(21) Appl. No.: 16/813,970

(22) Filed: Mar. 10, 2020

(65) Prior Publication Data

US 2020/0211238 A1 Jul. 2, 2020

Related U.S. Application Data

(63) Continuation of application No. PCT/JP2018/026122, filed on Jul. 11, 2018.

(30) Foreign Application Priority Data

Oct. 6, 2017 (JP) .............................. JP2017-196396

(51) Int. Cl.
*G06T 11/00* (2006.01)
*G01N 23/04* (2018.01)

(52) U.S. Cl.
CPC ............ *G06T 11/005* (2013.01); *G01N 23/04* (2013.01); *G01N 2223/401* (2013.01); *G01N 2223/423* (2013.01); *G06T 2211/408* (2013.01)

(58) Field of Classification Search
CPC ....... A61B 6/487; A61B 6/5205; A61B 6/482; A61B 6/4233; A61B 6/5258; G06T 5/20;
(Continued)

(56) References Cited

U.S. PATENT DOCUMENTS

| 4,542,459 A | 9/1985 | Riederer |
| 9,048,154 B2 | 6/2015 | Takenaka et al. |

(Continued)

FOREIGN PATENT DOCUMENTS

| JP | H0876302 A | 3/1996 |
| JP | 2015092913 A | 5/2015 |
| WO | 2017/073043 A1 | 5/2017 |

OTHER PUBLICATIONS

C. Amiot et al., Curvelet Based Contrast Enhancement in Fluoroscopic Sequences, IEEE Trans. Med. Imaging, vol. 34, No. 1, (2015) 137-47, XP011568793.

*Primary Examiner* — Brenda C Bernardi
(74) *Attorney, Agent, or Firm* — Venable LLP

(57) ABSTRACT

An image processing apparatus comprises a filtering unit for performing recursive filtering on a first signal component and a second signal component that are obtained by emitting radiation at a plurality of levels of energy toward an object, and a generation unit for generating a moving image based on the first signal component and the second signal component on which the recursive filtering is performed. A filter coefficient of the recursive filtering performed on the first signal component and a filter coefficient of the recursive filtering performed on the second signal component differ from each other.

14 Claims, 6 Drawing Sheets

(58) Field of Classification Search
CPC ......... G06T 5/50; G06T 5/002; G06T 11/005; G06T 2207/10121; G06T 2211/408; G06T 2207/30021; G06T 2207/10016; G01N 23/04; G01N 2223/423; G01N 2223/401

See application file for complete search history.

(56) References Cited

U.S. PATENT DOCUMENTS

| | | | |
|---|---|---|---|
| 9,128,196 B2 | 9/2015 | Sato et al. | |
| 9,134,432 B2 | 9/2015 | Iwashita et al. | |
| 9,234,966 B2 | 1/2016 | Sugawara et al. | |
| 9,423,512 B2 | 8/2016 | Sato et al. | |
| 9,445,030 B2 | 9/2016 | Yagi et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,470,802 B2 | 10/2016 | Okada et al. | |
| 9,541,653 B2 | 1/2017 | Iwashita et al. | |
| 9,655,586 B2 | 5/2017 | Yagi et al. | |
| 9,737,271 B2 | 8/2017 | Iwashita et al. | |
| 9,812,474 B2 | 11/2017 | Yagi et al. | |
| 9,820,711 B2 | 11/2017 | Tsukuda et al. | |
| 9,971,046 B2 | 5/2018 | Ryu et al. | |
| 9,980,685 B2 | 5/2018 | Iwashita et al. | |
| 9,989,656 B2 | 6/2018 | Sato et al. | |
| 10,009,990 B2 | 6/2018 | Takenaka et al. | |
| 10,070,082 B2 | 9/2018 | Tsukuda et al. | |
| 10,197,684 B2 | 2/2019 | Terui et al. | |
| 10,274,612 B2 | 4/2019 | Ishii et al. | |
| 10,441,238 B2 | 10/2019 | Terui et al. | |
| 2014/0239186 A1 | 8/2014 | Sato et al. | |
| 2014/0361189 A1 | 12/2014 | Kameshina et al. | |
| 2015/0063534 A1 | 3/2015 | Allmendinger et al. | |
| 2016/0270750 A1 | 9/2016 | Machida | |
| 2016/0270755 A1 | 9/2016 | Takenaka et al. | |
| 2018/0128755 A1 | 5/2018 | Iwashita et al. | |
| 2018/0317868 A1 | 11/2018 | Terui et al. | |
| 2018/0325476 A1* | 11/2018 | Machida | A61B 6/5205 |
| 2018/0328862 A1 | 11/2018 | Sato et al. | |
| 2019/0179036 A1 | 6/2019 | Takenaka et al. | |
| 2019/0320993 A1 | 10/2019 | Noda et al. | |
| 2019/0349541 A1 | 11/2019 | Iwashita et al. | |
| 2020/0124749 A1 | 4/2020 | Takenaka et al. | |
| 2020/0150059 A1 | 5/2020 | Torii et al. | |
| 2020/0150286 A1 | 5/2020 | Terui et al. | |
| 2020/0155097 A1 | 5/2020 | Torii et al. | |

* cited by examiner

F I G. 10
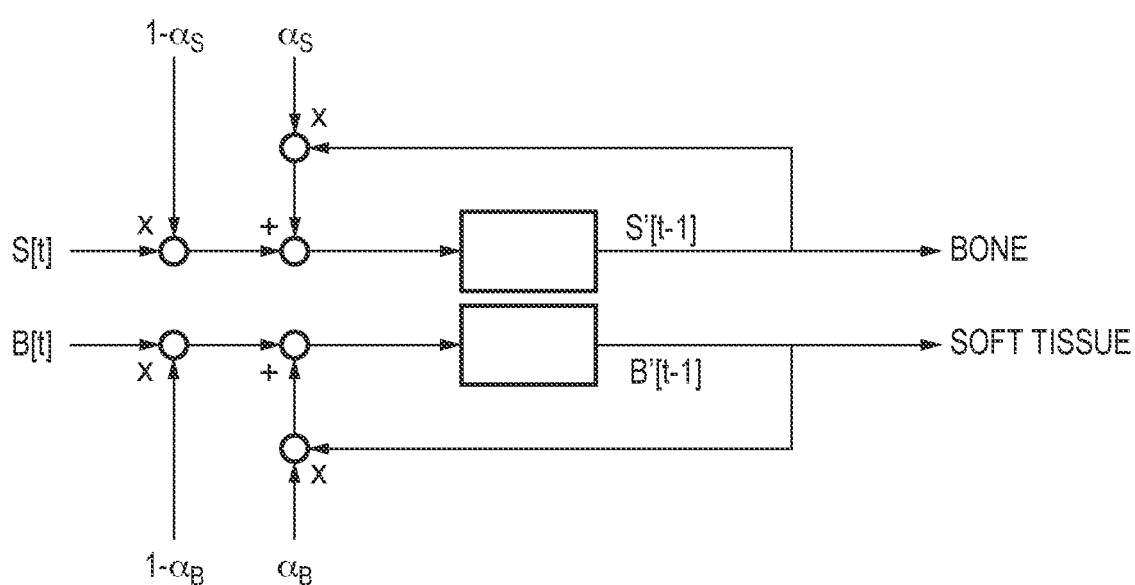

IMAGE PROCESSING APPARATUS, IMAGE PROCESSING METHOD, AND PROGRAM

CROSS-REFERENCE TO RELATED APPLICATIONS

This application is a Continuation of International Patent Application No. PCT/JP2018/026122, filed Jul. 11, 2018, which claims the benefit of Japanese Patent Application No. 2017-196396, filed Oct. 6, 2017, both of which are hereby incorporated by reference herein in their entirety.

BACKGROUND OF THE INVENTION

Field of the Invention

The present invention relates to an image processing apparatus, an image processing method, and a program.

Background Art

As imaging apparatuses that are used for medical image diagnosis and nondestructive inspection using radiation such as X-rays, radiation imaging apparatuses using a Flat Panel Detector (hereinafter abbreviated as FPD) that is made from a semiconductor material are becoming popular. One example of imaging methods using the FPD is energy subtraction. In energy subtraction, a plurality of images that are formed using radioactive rays having mutually different levels of energy are acquired by emitting radioactive rays at different tube voltages a plurality of times, for example. By performing computation on the images, processing for dividing an image of an object into a bone image and a soft tissue image can be performed, for example. PTL1 proposes a technology for reducing noise of the bone image and the soft tissue image by performing image processing for varying frequency characteristics of image signals.

When catheter surgery or the like is performed using the FPD, fluoroscopic radiography is performed. In fluoroscopic radiography, low dose radiation is used to reduce the exposure dose. However, if the dose of radiation is reduced, quantum noise of the radiation increases, and noise of images divided from an image of the object increases. The technology described in PTL1 does not mention a reduction of the noise, and there is demand that various measures be taken for this issue. The present invention provides a technology for improving quality of an image generated using radiation at a plurality of levels of energy.

CITATION LIST

Patent Literature

PTL1: Japanese Patent Laid-Open No. 8-76302

SUMMARY OF THE INVENTION

In view of the above-described problem, provided is an image processing apparatus including a filtering unit configured to perform recursive filtering on a first signal component and a second signal component that are obtained by emitting radiation at a plurality of levels of energy toward an object, and a generation unit configured to generate a moving image based on the first signal component and the second signal component on which the recursive filtering is performed, wherein a filter coefficient of the recursive filtering performed on the first signal component and a filter coefficient of the recursive filtering performed on the second signal component differ from each other.

Further features of the present invention will become apparent from the following description of exemplary embodiments with reference to the attached drawings.

BRIEF DESCRIPTION OF THE DRAWINGS

FIG. 10 is a diagram showing some operations of the control apparatus of the second embodiment.

DESCRIPTION OF THE EMBODIMENTS

The following describes embodiments of the present invention with reference to the accompanying drawings. Through various embodiments, similar elements are denoted with the same reference signs, and a redundant description thereof is omitted. The embodiments can be appropriately changed or combined. In the following description, radiation includes α-rays, β-rays, γ-rays, etc. that are beams formed by particles (including photons) that are emitted through radioactive decay, as well as beams that have substantially equivalent or higher levels of energy, such as X-rays, particle beams, and cosmic rays.

First Embodiment

Figure 1:
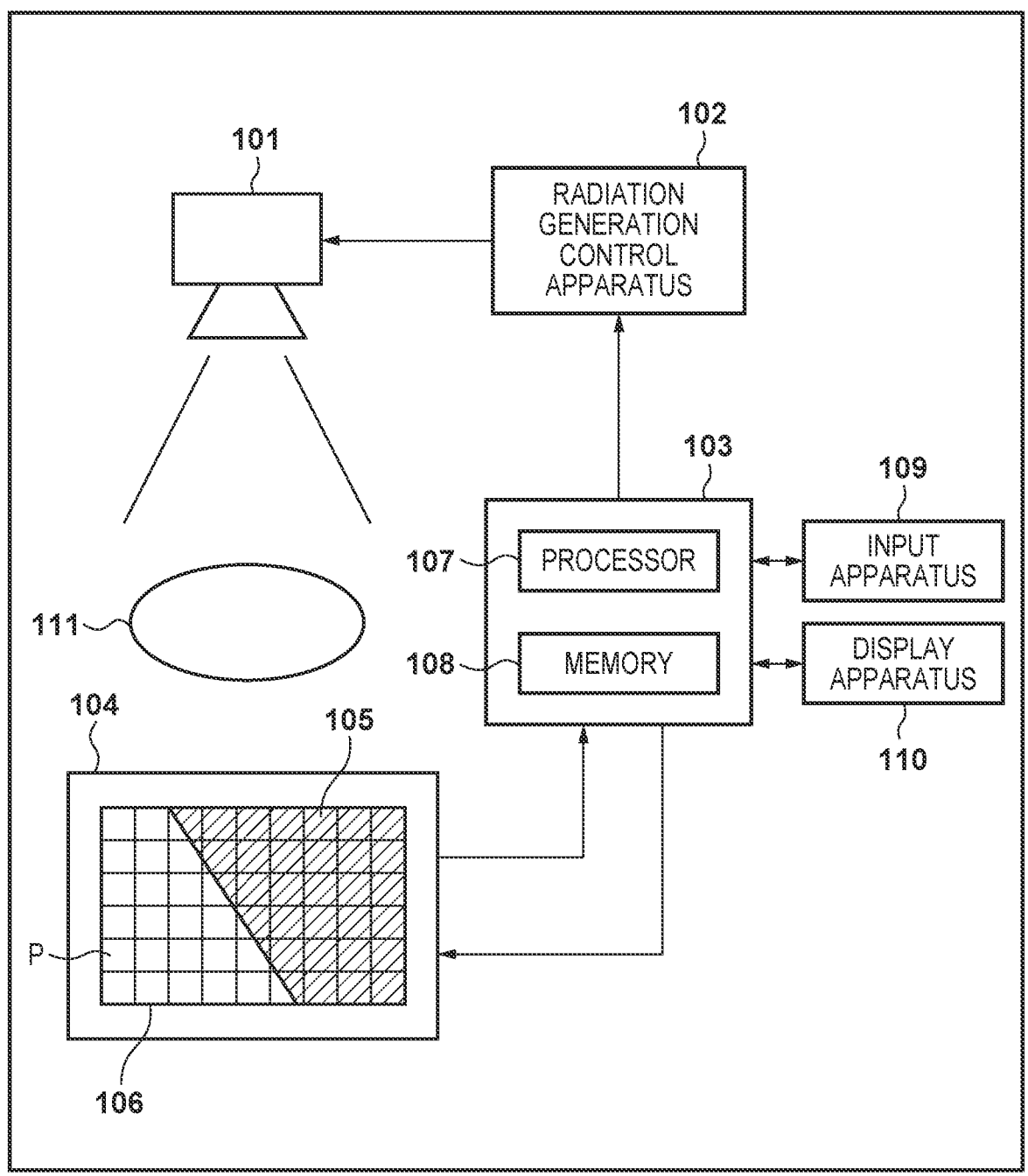
FIG. 1 is a diagram showing an example of a configuration of a radiation imaging system of each embodiment.

FIG. 1 shows a block diagram of a radiation imaging system according to the present embodiment. The radiation imaging system is used for still image capturing, such as general image capturing performed in medical diagnosis, and moving image capturing, such as fluoroscopic radiography, for example. The radiation imaging system is constituted by a radiation generating apparatus 101, a radiation generation control apparatus 102, a control apparatus 103, and a radiation imaging apparatus 104.

The radiation generation control apparatus 102 controls the radiation generating apparatus 101 to emit radiation toward the radiation imaging apparatus 104. The radiation imaging apparatus 104 is constituted by a scintillator 105 that converts radiation to visible light and a two-dimensional detector 106 that detects visible light. The two-dimensional detector 106 is a sensor in which pixels P that detect radiation quanta are arranged in an array constituted by X columns and Y rows, and outputs image information.

The control apparatus 103 controls other apparatuses in the radiation imaging system. Furthermore, as described later in detail, the control apparatus 103 performs image processing for generating an output moving image based on a plurality of input moving images that are obtained by emitting radiation at a plurality of levels of energy toward the same object. Therefore, the control apparatus 103 also functions as an image processing apparatus. Alternatively, functions of the control apparatus 103 relating to image processing may also be implemented as a separate image processing apparatus. For example, a configuration may also be employed in which images acquired by the control apparatus 103 are transferred to a separate image processing apparatus via medical PACS, and an image is displayed after energy subtraction processing is performed by this image processing apparatus.

The control apparatus 103 is a computer that includes a processor 107 and a memory 108. The processor 107 is constituted by a CPU, for example, and the memory 108 is constituted by a ROM and a RAM, for example. Processing performed by the control apparatus 103 is executed as a result of the processor 107 executing a program read into the memory 108. Alternatively, processing performed by the control apparatus 103 may also be executed by a dedicated circuit, such as an ASIC or a FPGA.

An input apparatus 109 and a display apparatus 110 are connected to the control apparatus 103. The input apparatus 109 is an apparatus for accepting input from a user of the radiation imaging system, and is constituted by a keyboard, a mouse, a touch pad, etc., for example. The display apparatus 110 is an apparatus for displaying information to the user of the radiation imaging system, and is constituted by a display, etc., for example. The input apparatus 109 and the display apparatus 110 may be configured together as a touch screen.

Figure 2:
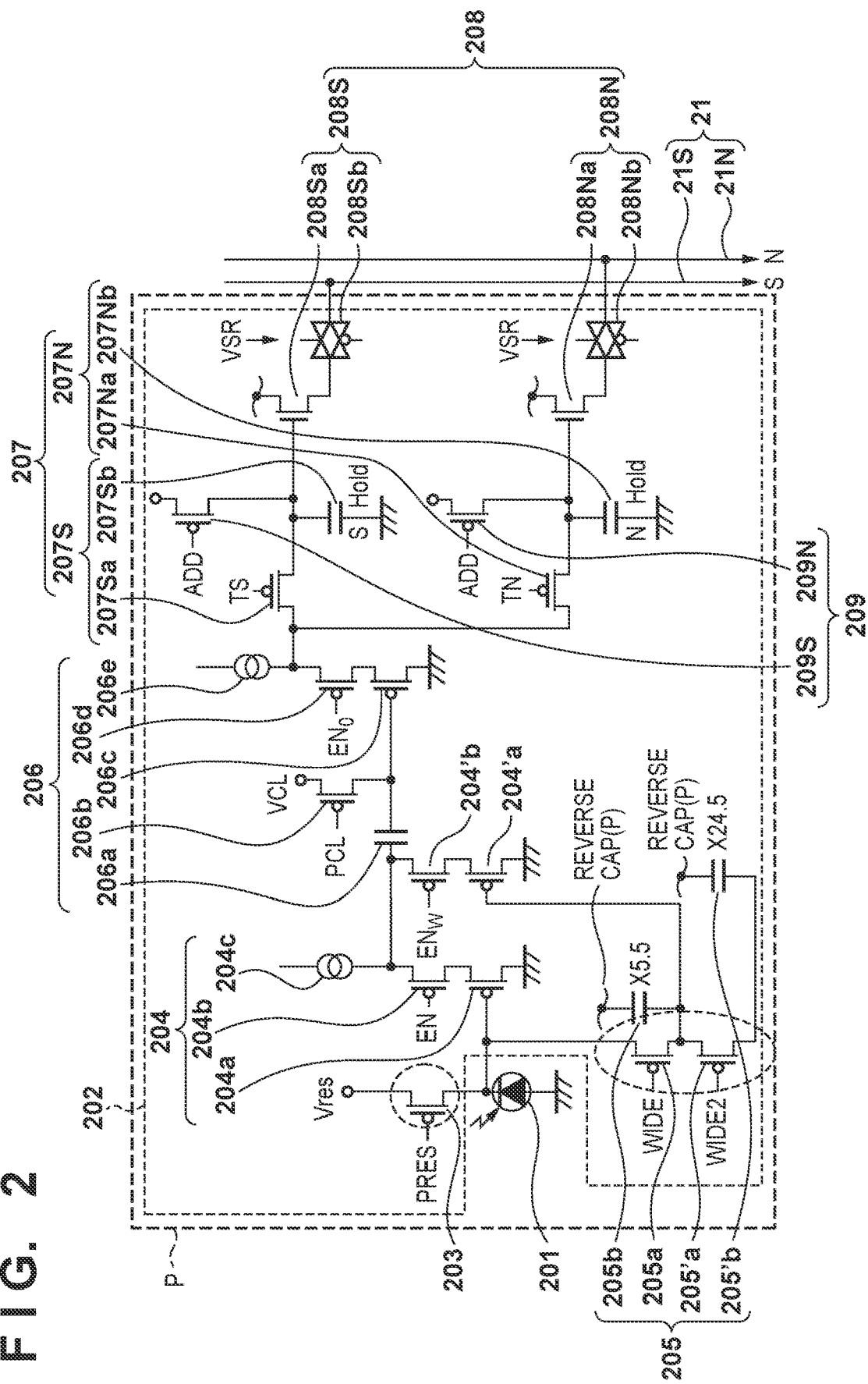
FIG. 2 is a diagram showing an example of a configuration of a pixel of each embodiment.

FIG. 2 shows an equivalent circuit schematic of a pixel P shown in FIG. 1. The pixel P includes a photoelectric conversion element 201 and an output circuit unit 202. The photoelectric conversion element 201 may be typically a photodiode. The output circuit unit 202 includes an amplifier circuit unit 204, a clamping circuit unit 206, a sample hold circuit unit 207, and a selection circuit unit 208.

The photoelectric conversion element 201 includes a charge storage unit. The charge storage unit is connected to the gate of a MOS transistor 204a of the amplifier circuit unit 204. The source of the MOS transistor 204a is connected to a current source 204c via a MOS transistor 204b. The MOS transistor 204a and the current source 204c constitute a source follower circuit. The MOS transistor 204b is an enable switch that is switched ON to cause the source follower circuit enter an operating state, when an enable signal EN supplied to the gate of the MOS transistor 204b is changed to an active level.

In the example shown in FIG. 2, the charge storage unit of the photoelectric conversion element 201 and the gate of the MOS transistor 204a constitute a common node. This node functions as a charge voltage conversion unit that converts a charge stored in the charge storage unit to a voltage. That is, a voltage V (=Q/C) that is determined by a charge Q stored in the charge storage unit and a capacitance value C of the charge voltage conversion unit appears in the charge voltage conversion unit. The charge voltage conversion unit is connected to a reset potential Vres via a reset switch 203. When a reset signal PRES is changed to an active level, the reset switch 203 is switched ON and the potential of the charge voltage conversion unit is reset to the reset potential Vres.

The clamping circuit unit 206 performs clamping on noise that is output by the amplifier circuit unit 204 according to the reset potential of the charge voltage conversion unit, by using a clamp capacitor 206a. That is, the clamping circuit unit 206 is a circuit for cancelling this noise from a signal that is output from the source follower circuit according to a charge generated through photoelectric conversion in the photoelectric conversion element 201. This noise includes kTC noise at the time of reset. Clamping is performed by switching a MOS transistor 206b ON by changing a clamp signal PCL to an active level, and thereafter switching the MOS transistor 206b OFF by changing the clamp signal PCL to a non-active level. The output side of the clamp capacitor 206a is connected to the gate of a MOS transistor 206c. The source of the MOS transistor 206c is connected to a current source 206e via a MOS transistor 206d. The MOS transistor 206c and the current source 206e constitute a source follower circuit. The MOS transistor 206d is an enable switch that is switched ON to cause the source follower circuit enter an operating state, when an enable signal $EN_0$ supplied to the gate of the MOS transistor 206d is changed to an active level.

A signal that is output from the clamping circuit unit 206 according to the charge generated through photoelectric conversion in the photoelectric conversion element 201 is written as an optical signal into a capacitor 207Sb via a switch 207Sa as a result of an optical signal sampling signal TS being changed to an active level. A signal that is output from the clamping circuit unit 206 when the MOS transistor 206b is switched ON immediately after the potential of the charge voltage conversion unit is reset is a clamp voltage. This noise signal is written into a capacitor 207Nb via a switch 207Na as a result of a noise sampling signal TN being changed to an active level. This noise signal includes an offset component of the clamping circuit unit 206. The switch 207Sa and the capacitor 207Sb constitute a signal sample hold circuit 207S and the switch 207Na and the capacitor 207Nb constitute a noise sample hold circuit 207N. The sample hold circuit unit 207 includes the signal sample hold circuit 207S and the noise sample hold circuit 207N.

When a drive circuit unit drives a row selection signal to an active level, the signal (optical signal) held by the capacitor 207Sb is output to a signal line 21S via a MOS transistor 208Sa and a row selection switch 208Sb. At the same time, the signal (noise) held by the capacitor 207Nb is output to a signal line 21N via a MOS transistor 208Na and a row selection switch 208Nb. The MOS transistor 208Sa constitutes a source follower circuit together with a constant current source (not shown) provided on the signal line 21S. Likewise, the MOS transistor 208Na constitutes a source follower circuit together with a constant current source (not shown) provided on the signal line 21N. The signal line 21S and the signal line 21N will be collectively referred to as a signal line 21. The MOS transistor 208Sa and the row selection switch 208Sb constitute a signal selection circuit unit 208S, and the MOS transistor 208Na and the row selection switch 208Nb constitute a noise selection circuit unit 208N. The selection circuit unit 208 includes the signal selection circuit unit 208S and the noise selection circuit unit 208N.

The pixel P may also include an addition switch 209S that adds optical signals of a plurality of pixels P adjacent to each other. In an addition mode, an addition mode signal ADD is changed to an active level, and the addition switch 209S is switched ON. As a result, capacitors 207Sb of adjacent pixels P are connected to each other via the addition switch 209S, and optical signals are averaged. Likewise, the pixel P may also include an addition switch 209N that adds noise of a plurality of pixels P adjacent to each other. When the addition switch 209N is switched ON, capacitors 207Nb of adjacent pixels P are connected to each other via the addition switch 209N, and noise is averaged. An addition unit 209 includes the addition switch 209S and the addition switch 209N.

The pixel P may also include a sensitivity changing unit 205 for changing sensitivity. For example, the pixel P may include a first sensitivity change switch 205a, a second sensitivity change switch 205'a, and circuit elements accompanying these switches. When a first change signal WIDE is changed to an active level, the first sensitivity change switch 205a is switched ON, and the capacitance value of a first additional capacitor 205b is added to the capacitance value of the charge voltage conversion unit. Thus, sensitivity of the pixel P is lowered. When a second change signal WIDE2 is changed to an active level, the second sensitivity change switch 205'a is switched ON, and the capacitance value of a second additional capacitor 205'b is added to the capacitance value of the charge voltage conversion unit. Thus, sensitivity of the pixel P is further lowered. If a function for lowering sensitivity of the pixel P is added as described above, a larger quantity of light can be received, and the dynamic range is widened. If the first change signal WIDE is changed to the active level, a MOS transistor 204'a may also be caused to perform a source follower operation, instead of the MOS transistor 204a, by changing an enable signal $EN_W$ to an active level. The MOS transistor 204'a is connected to the clamp capacitor 206a via a MOS transistor 204'b.

The radiation imaging apparatus 104 reads the output of the above-described pixel P, converts the output to a digital value using an AD converter (not shown), and then transfers an image to the control apparatus 103. In a case in which the radiation imaging system captures a moving image, images are periodically transferred as frames from the radiation imaging apparatus 104 to the control apparatus 103. That is, a moving image is transferred from the radiation imaging apparatus 104 to the control apparatus 103. In the present embodiment, a moving image means chronological images.

Figure 3:
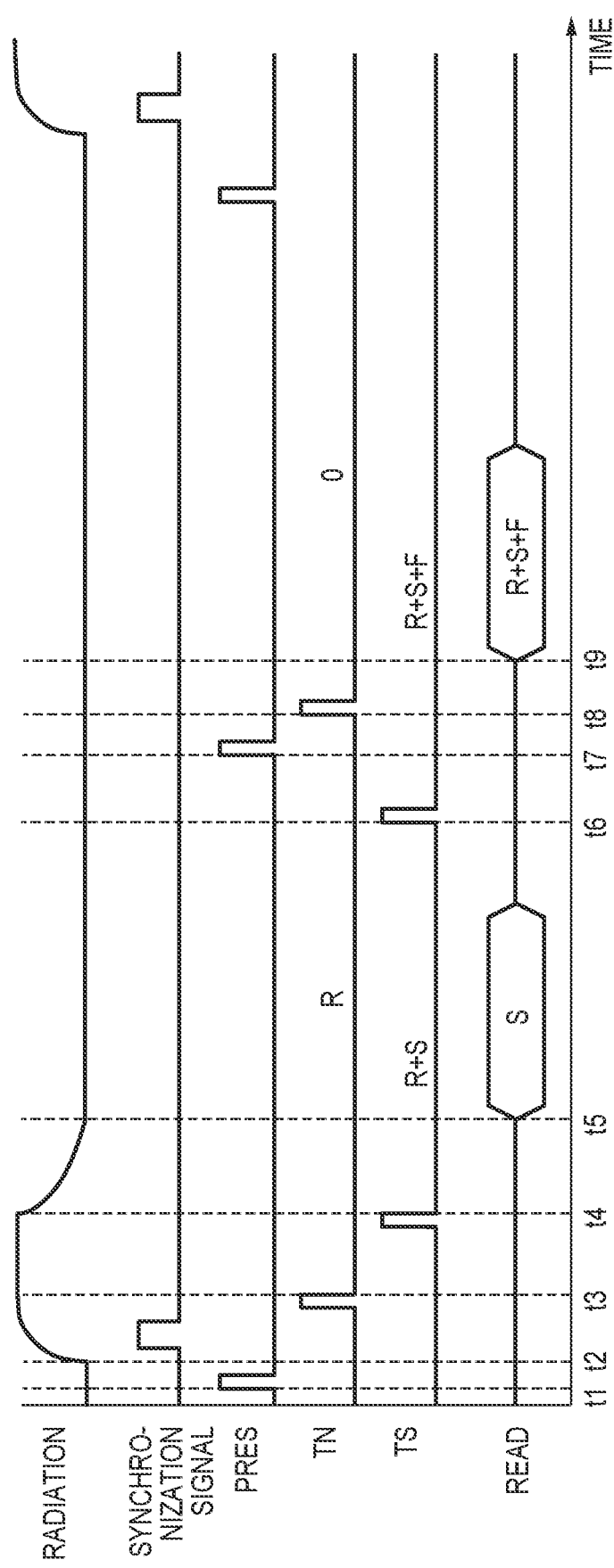
FIG. 3 is a diagram showing a frame operation of each embodiment.

Driving timings for performing energy subtraction in the radiation imaging system of the present embodiment will be described with reference to FIG. 3. "Radiation" shows the dose of radiation emitted toward the radiation imaging apparatus 104. "Synchronization signal" is a signal that is supplied by the control apparatus 103 to the radiation imaging apparatus 104. "PRES" is the reset signal described with reference to FIG. 2. "TS" is the optical signal sampling signal TS described with reference to FIG. 2. "TN" is the noise sampling signal TN described with reference to FIG. 2.

At time t1, the control apparatus 103 resets the photoelectric conversion element 201. At time t2, the control apparatus 103 starts emission of radiation. The tube voltage of radiation ideally has a rectangular waveform, but it takes finite times for the tube voltage to rise and fall. In particular, if pulsed radiation is emitted for a short period of time, the tube voltage has a waveform as shown in FIG. 3, which cannot be considered a rectangular waveform. That is, energy of the radiation varies between a rise period (time t2 to time t3), a stable period (time t3 to time t4), and a fall period (time t4 to time t5). As described above, in the present embodiment, radiation is emitted at a plurality of levels of energy in a single emission of radiation.

At time t3 (the end of the radiation rise period), the control apparatus 103 performs sampling using the noise sample hold circuit 207N. As a result, a signal R that is obtained using radiation of the rise period is held by the noise sample hold circuit 207N. At time t4 (the end of the radiation stable period), the control apparatus 103 performs sampling using the signal sample hold circuit 207S. As a result, a sum of the signal R and a signal S that is obtained using radiation of the stable period is held by the signal sample hold circuit 207S.

At time t5, a reading circuit (not shown) of the radiation imaging apparatus 104 transmits, as an image, a difference between a signal read from the signal line 21N and a signal read from the signal line 21S to the control apparatus 103. Since the signal R is held by the noise sample hold circuit 207N and the sum of the signal R and the signal S is held by the signal sample hold circuit 207S, the reading circuit outputs the signal S.

After emission of radiation and reading of the signal S are complete, at time t6, the control apparatus 103 performs sampling using the signal sample hold circuit 207S again. As a result, a sum of the signal R, the signal S, and a signal F that is obtained using radiation of the fall period is held by the signal sample hold circuit 207S. At time t7, the control apparatus 103 resets the photoelectric conversion element 201. At time t8, the control apparatus 103 performs sampling using the signal sample hold circuit 207S again. As a result, a signal (in this example, 0) at the time of reset is held by the signal sample hold circuit 207S. At time t9, the reading circuit of the radiation imaging apparatus 104 transmits, as an image, a difference between a signal read from the signal line 21N and a signal read from the signal line 21S to the control apparatus 103. Since 0 is held by the noise sample hold circuit 207N and the sum of the signal R, the signal S, and the signal F is held by the signal sample hold circuit 207S, the reading circuit outputs the sum of the signal R, the signal S, and the signal F. The control apparatus 103 can calculate a sum of the signal R obtained using radiation of the rise period and the signal F obtained using radiation of the fall period, by calculating a difference between the two transmitted images. An image represented by the signal S and an image represented by the sum of the signal R and the signal F correspond to images that are obtained using radiation at mutually different levels of energy. Therefore, the control apparatus 103 can perform energy subtraction by performing computation on the images.

Timings for resetting the sample hold circuit unit 207 and the photoelectric conversion element 201 are determined using a synchronization signal 307 that indicates that emission of radiation from the radiation generating apparatus 101 is started. As a method for detecting the start of emission of radiation, a configuration may be employed in which the tube current of the radiation generating apparatus 101 is measured, and it is determined whether or not the current value is higher than a preset threshold value. Alternatively, a configuration may also be employed in which, after the photoelectric conversion element 201 is reset, signals are repeatedly read from the pixel P, and it is determined whether or not the pixel value is higher than a preset threshold value. A configuration may also be employed in which a radiation detector other than the two-dimensional detector 106 is incorporated in the radiation imaging apparatus 104, and it is determined whether or not a measurement value obtained by the radiation detector is higher than a preset threshold value. In any of these cases, after a prescribed period has elapsed from input of the synchronization signal 307, the radiation imaging apparatus 104 performs sampling using the signal sample hold circuit 207S, performs sampling using the noise sample hold circuit 207N, and resets the photoelectric conversion element 201.

Figure 4:
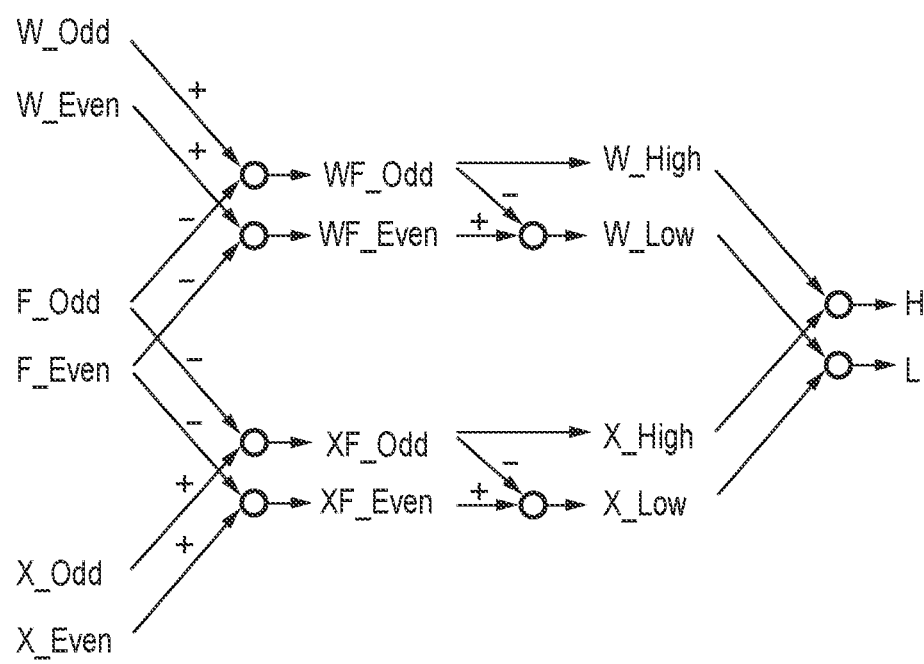
FIG. 4 is a diagram showing some operations of a control apparatus of each embodiment.

Next, a method of energy subtraction will be described. Energy subtraction in the present embodiment is divided into three steps, namely, correction, signal processing, and image processing. A correction method performed in energy subtraction processing in the present embodiment will be described with reference to FIG. 4. The control apparatus 103 acquires the two images described with reference to FIG. 3 by performing imaging without emitting radiation toward the radiation imaging apparatus 104. An image represented by the signal S is denoted as F_Odd, and an image represented by the sum of the signal R, the signal S, and the signal F is denoted as F_Even. These images correspond to fixed pattern noise (FPN) of the radiation imaging apparatus 104.

Next, the control apparatus 103 acquires the two images described with reference to FIG. 3 by performing imaging by emitting radiation toward the radiation imaging apparatus 104 in a state in which an object 111 is not arranged. An image represented by the signal S is denoted as W_Odd, and an image represented by the sum of the signal R, the signal S, and the signal F is denoted as W_Even. These images correspond to sums of the fixed pattern noise (FPN) of the radiation imaging apparatus 104 and the signals obtained using radiation. By subtracting F_Odd from W_Odd and subtracting F_Even from W_Even, WF_Odd and WF_Even from which the FPN has been removed are obtained.

WF_Odd is an image represented by the signal S obtained using radiation of the stable period, and WF_Even is an image represented by the sum of the signal R, the signal S, and the signal F respectively obtained using radiation of the rise period, the stable period, and the fall period. Radiation of the stable period has higher energy than radiation of the rise period and radiation of the fall period. Accordingly, the control apparatus 103 takes WF_Odd as a high-energy image W_High in a case in which the object 111 is absent, and takes an image that is obtained by subtracting WF_Odd from WF_Even (i.e., an image represented by a sum of the signal R and the signal F) as a low-energy image W_Low in the case in which the object 111 is absent.

Next, the control apparatus 103 acquires the two images described with reference to FIG. 3 for each frame period by capturing a moving image by emitting radiation toward the radiation imaging apparatus 104 in a state in which the object 111 is arranged. Thus, the control apparatus 103 acquires a plurality of input moving images obtained by emitting radiation at a plurality of levels of energy toward the same object 111. An image represented by the signal S is denoted as X_Odd, and an image represented by the sum of the signal R, the signal S, and the signal F is denoted as X_Even. These images correspond to sums of the fixed pattern noise (FPN) of the radiation imaging apparatus 104 and the signals obtained using radiation. By subtracting F_Odd from X_Odd and subtracting F_Even from X_Even, XF_Odd and XF_Even from which the FPN has been removed are obtained. Thereafter, similarly to the case in which the object 111 is absent, the control apparatus 103 takes XF_Odd as a high-energy image X_High in a case in which the object 111 is present. Also, the control apparatus 103 takes an image that is obtained by subtracting XF_Odd from XF_Even (i.e., an image represented by the sum of the signal R and the signal F) as a low-energy image X_Low in the case in which the object 111 is present.

When d represents the thickness of the object 111, $\mu$ represents the linear attenuation coefficient of the object 111, $I_0$ represents the pixel value in the case in which the object 111 is absent, and I represents the pixel value in the case in which the object 111 is present, the following equation holds.

$$I = I_0 \exp(\mu d) \quad (1)$$

The following equation is obtained by transforming equation (1).

$$I/I_0 = \exp(\mu d) \quad (2)$$

The right side of equation (2) indicates the attenuation ratio of the object 111. The attenuation ratio of the object 111 is a real number between 0 to 1. Therefore, the control apparatus 103 computes an image L at an attenuation ratio of low energy by dividing the low-energy image X_Low in the case in which the object 111 is present by the low-energy image W_Low in the case in which the object 111 is absent. Likewise, the control apparatus 103 computes an image H at an attenuation ratio of high energy by dividing the high-energy image X_High in the case in which the object 111 is present by the high-energy image W_High in the case in which the object 111 is absent.

Figure 5:
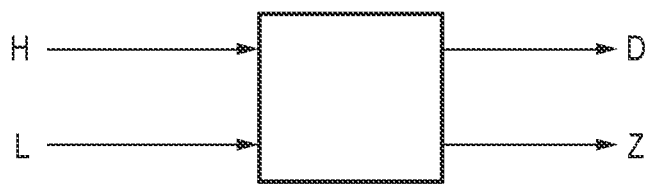
FIG. 5 is a diagram showing some operations of a control apparatus of a first embodiment.

Next, a signal processing method performed in energy subtraction in the present embodiment will be described with reference to FIG. 5. The control apparatus 103 computes an image that represents an effective atomic number Z and an image that represents a surface density D from the image L and the image H obtained through the processing shown in FIG. 4. The image L and the image H are based on the plurality of input moving images that the control apparatus 103 acquired from the radiation imaging apparatus 104, and accordingly the control apparatus 103 generates an image representing the effective atomic number Z and a second image representing the surface density D using the plurality of input moving images. The effective atomic number Z is an equivalent atomic number of a mixture. The surface density D is a product of the density [g/cm$^3$] of the object 111 and the thickness [cm] of the object 111, and the dimension of the surface density D is [g/cm$^2$].

When E represents energy of radiation photons, N (E) represents the photon number at the energy E, Z represents the effective atomic number, D represents the surface density, $\mu$ (Z, E) represents the mass attenuation coefficient at the effective atomic number Z and the energy E, and I/I$_0$ represents the attenuation ratio, the following equation holds.

$$\frac{\int_0^\infty N(E) \exp\{-\mu(Z, E)D\} E dE}{\int_0^\infty N(E) E dE} \quad (3)$$

The photon number N (E) at the energy E is the spectrum of radiation. The spectrum of radiation is obtained through simulation or actual measurement. Also, the mass attenuation coefficient $\mu$(Z, E) at the effective atomic number Z and the energy E is obtained from a database of NIST (National Institute of Standards and Technology), for example. Namely, the attenuation ratio I/I$_0$ at a given effective atomic number Z, a given surface density D, and a given spectrum N (E) of radiation can be calculated.

When N$_L$ (E) represents the spectrum of radiation of the rise period and the fall period and N$_H$ (E) represents the spectrum of radiation of the stable period, the following two equations hold.

$$L = \frac{\int_0^\infty N_L(E)\exp\{-\mu(Z, E)D\}EdE}{\int_0^\infty N_L(E)EdE}$$

$$H = \frac{\int_0^\infty N_H(E)\exp\{-\mu(Z, E)D\}EdE}{\int_0^\infty N_H(E)EdE} \quad (4)$$

Equations (4) are nonlinear simultaneous equations. By solving the simultaneous equations using the Newton-Raphson method, for example, the control apparatus 103 can compute the image representing the effective atomic number Z and the image representing the surface density D from the image L at the attenuation ratio of low energy and the image H at the attenuation ratio of high energy.

Figure 6:
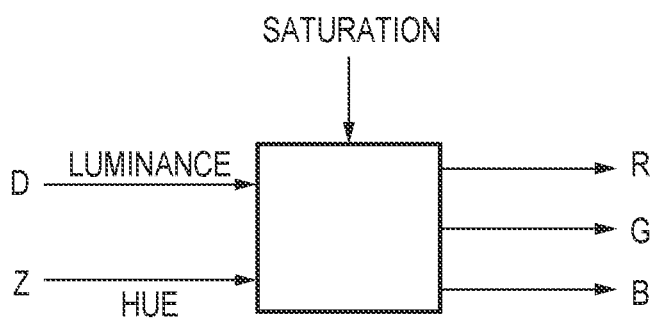
FIG. 6 is a diagram showing some operations of the control apparatus of the first embodiment.

An image processing method performed in energy subtraction processing in the present embodiment will be described with reference to FIG. 6. In image processing performed in the present embodiment, the control apparatus 103 determines values of two parameters that constitute a frame based on the image representing the effective atomic number Z and the image representing the surface density D. A prescribed value is used as the value of the remaining one parameter that constitutes the frame.

In the present embodiment, an output moving image is a color moving image, and the three parameters are components of a color space. The color space is an HLS color space or an HSV color space, for example. The following describes an example in which the color space is an HLS color space. The HLS color space is constituted by three components, namely, hue, saturation, and luminance. The control apparatus 103 determines hue and luminance based on the above-described plurality of input moving images and determines saturation based on the prescribed value.

For example, the control apparatus 103 determines the value of hue based on the image representing the effective atomic number Z and determines the value of luminance based on the image representing the surface density D. Specifically, the control apparatus 103 converts the effective atomic number Z to hue using a function (e.g., a linear function) according to which the minimum value and the maximum value of the effective atomic number Z are respectively mapped to the minimum value and the maximum value of hue. Luminance is determined in a similar manner. Further, the control apparatus 103 uses a prescribed value as saturation. The prescribed value of saturation may be stored in the memory 108 when the control apparatus 103 is manufactured, for example.

The control apparatus 103 generates a frame using hue, saturation, and luminance determined as described above, and causes the display apparatus 110 to display the frame. The control apparatus 103 generates and displays an output moving image by periodically generating and displaying frames.

In the above-described example, the value of hue and the value of luminance are determined based on frames of input moving images, and the value of saturation is a prescribed value. Alternatively, a configuration is also possible in which the value of saturation and the value of luminance are determined based on frames of input moving images, and the value of hue is a prescribed value. Further, a configuration is also possible in which the value of hue and the value of saturation are determined based on frames of input moving images, and the value of luminance is a prescribed value. In a case in which an HSV color space is used for generating a frame, any of the values of hue, saturation, and brightness may be a prescribed value.

Figure 7:
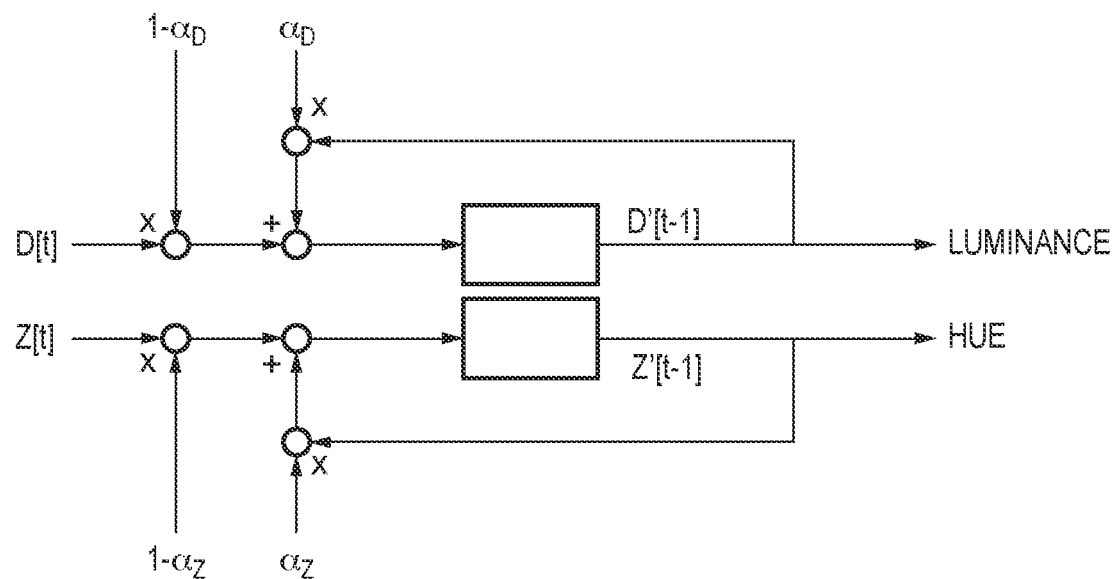
FIG. 7 is a diagram showing some operations of the control apparatus of the first embodiment.

Next, filtering performed in the present embodiment will be described with reference to FIG. 7. In order to reduce noise of hue and noise of luminance, the control apparatus 103 performs filtering on a moving image representing the effective atomic number Z and a moving image representing the surface density D. These moving images could be called two moving images obtained by emitting radiation at a plurality of levels of energy toward the same object 111. The control apparatus 103 generates an output moving image based on these moving images. The filtering performed by the control apparatus 103 may include filtering in a time direction, filtering in a spatial direction, or both of these. The control apparatus 103 generates the above-described output moving image based on the two moving images subjected to the filtering.

First, a case will be described in which the control apparatus 103 performs filtering in a time direction on the moving image representing the effective atomic number Z and the moving image representing the surface density D. Processing that is performed using a recursive filter will be described as one example of filtering in the time direction. Assume that Z[t] represents the effective atomic number in the t-th frame, Z'[t−1] represents the effective atomic number in the t−1-th frame after application of the recursive filter, and $\alpha_Z$ represents the coefficient of the recursive filter for the effective atomic number. The control apparatus 103 calculates the effective atomic number Z'[t] in the t-th frame after application of the recursive filter, using the following equation.

$$Z'[t]=\alpha_Z *Z'[t-1]+(1-\alpha_Z)*Z[t] \quad (5)$$

Likewise, assume that D[t] represents the surface density in the t-th frame, D'[t−1] represents the surface density in the t−1-th frame after application of the recursive filter, and $\alpha_D$ represents the coefficient of the recursive filter for the surface density. The control apparatus 103 calculates the surface density D'[t] in the t-th frame after application of the recursive filter, using the following equation.

$$D'[t]=\alpha_D *D'[t-1]+(1-\alpha_D)*D[t] \quad (6)$$

As described above, a filtering unit of the control apparatus 103 performs recursive filtering on a first signal component and a second signal component that are obtained by emitting radiation at a plurality of levels of energy toward the object. Thereafter, a generation unit of the control apparatus 103 generates a moving image based on the first signal component and the second signal component subjected to the recursive filtering. The coefficients $\alpha_Z$ and $\alpha_D$ of the recursive filters are real numbers between 0 and 1. As a filter coefficient is increased, averaging of pixel values is performed going further back to the past, and accordingly noise is reduced. However, if the filter coefficient is too large, image lag occurs in a portion in which the object has moved.

In the case of an object of some type, the moving image representing the effective atomic number Z shows a smaller change in the time direction than the moving image representing the surface density D shows. Therefore, if the coefficient $\alpha_Z$ of the recursive filter for the effective atomic number Z is made larger than the coefficient $\alpha_D$ of the recursive filter for the surface density D, image lag can be suppressed while the noise of hue is reduced. As a result, visibility of the moving image can be improved. In the case of an object of another type, visibility of the moving image can be improved by making the coefficient $\alpha_Z$ of the recursive filter for the effective atomic number Z smaller than the coefficient $\alpha_D$ of the recursive filter for the surface density D. As described above, visibility of the moving image can be improved by individually setting filter coefficients such that the filter coefficient of filtering performed on the moving image representing the effective atomic number Z differs from the filter coefficient of filtering performed on the moving image representing the surface density D. As described above, in the present embodiment, the filter coefficient of recursive filtering performed on the first signal component differs from the filter coefficient of recursive filtering performed on the second signal component.

Next, a method for determining the filter coefficients $\alpha_Z$ and $\alpha_D$ will be described. If the coefficient of a recursive filter is large, image lag is likely to occur in a portion in which the object 111 has moved. Therefore, the control apparatus 103 detects movement of the object 111 and reduces the recursive filter coefficient. The control apparatus 103 determines that the object 111 has moved if the absolute value of a difference in the pixel value between the current frame and the immediately preceding frame is larger than a preset threshold value, for example.

In the case of an object of some type, the moving image representing the effective atomic number Z has larger noise in the time direction than the moving image representing the surface density D has. Accordingly, if movement of the object 111 is detected using the moving image representing the effective atomic number Z when determining a coefficient $\alpha_Z[t]$ of the recursive filter for the effective atomic number in the t-th frame, it is highly likely that an erroneous determination will be made due to noise. Therefore, the control apparatus 103 detects movement of the object 111 using the moving image representing the surface density D. For example, assume that D[t] represents the surface density in the t-th frame and D'[t−1] represents the surface density in the t−1-th frame after application of the recursive filter. Also, $\alpha_Z[t]$ represents the coefficient of the recursive filter for the effective atomic number in the t-th frame, $\alpha_D[t]$ represents the coefficient of the recursive filter for the surface density in the t-th frame, and T represents a preset threshold value. The control apparatus 103 determines coefficients of the recursive filters using the following equations.

$$\alpha_D[t] = \alpha_D(|D[t]-D'[t-1]| \leq T)$$

$$\alpha_D[t] = 0 (|D[t]-D'[t-1]| > T)$$

$$\alpha_Z[t] = \alpha_Z(|D[t]-D'[t-1]| \leq T)$$

$$\alpha_Z[t] = 0 (|D[t]-D'[t-1]| > T) \quad (7)$$

According to these equations, the control apparatus 103 determines the filter coefficient $\alpha_Z[t]$ for the moving image representing the effective atomic number Z based on a change in the image of the object 111 in the time direction in the moving image representing the surface density D. Namely, a determination unit of the control apparatus 103 determines a filter coefficient for the second signal component based on a change in the first signal component in the time direction. In this example, the first signal component represents the surface density D and the second signal component represents the effective atomic number Z. Furthermore, the control apparatus 103 determines the filter coefficient $\alpha_D[t]$ for the moving image representing the surface density D based on a change in the image of the object 111 in the time direction in the moving image representing the surface density D. Namely, the determination unit of the control apparatus 103 determines a filter coefficient for the first signal component based on a change in the first signal component in the time direction. Through the above-described processing, image lag is suppressed in a case in which the object 111 has moved, and accordingly noise of the moving image representing the effective atomic number Z can be reduced by applying a larger filter coefficient.

In the above-described example, filtering is performed using the recursive filter, but filtering for averaging pixel values of the past N frames may also be performed as filtering in the time direction. In this filtering, the filter coefficient is the number N of frames that are averaged.

In the above-described example, filter coefficients are changed based on a change in the image of the object in the time direction. Alternatively, the control apparatus 103 may also change filter coefficients based on a change in the image of the object in the spatial direction. A change in the spatial direction is determined based on an edge or a spatial frequency of the object, for example. For example, when D[x, y, t] represents the surface density at a coordinate (x, y) in the t-th frame, the control apparatus 103 determines coefficients of the recursive filters using the following equations.

$$\alpha_D[x,y,t] = \alpha_D(|D[x,y,t]-D[x-1,y,t]| \leq T)$$

$$\alpha_D[x,y,t] = 0(|D[x,y,t]-D[x-1,y,t]| > T)$$

$$\alpha_Z[x,y,t] = \alpha_D(|D[x,y,t]-D[x-1,y,t]| \leq T)$$

$$\alpha_Z[x,y,t] = 0(|D[x,y,t]-D[x-1,y,t]| > T) \quad (8)$$

According to these equations, the control apparatus 103 determines the filter coefficient $\alpha_Z[x, y, t]$ for the moving image representing the effective atomic number Z based on a change in the image of the object 111 in the spatial direction in the moving image representing the surface density D. Namely, the determination unit of the control apparatus 103 determines a filter coefficient for the second signal component based on a change in the first signal component in the spatial direction. Furthermore, the control apparatus 103 determines the filter coefficient $\alpha_D[x, y, t]$ for the moving image representing the surface density D based on a change in the image of the object 111 in the spatial direction in the moving image representing the surface density D. Namely, the determination unit of the control apparatus 103 determines a filter coefficient for the first signal component based on a change in the first signal component in the spatial direction.

Next, a case will be described in which the control apparatus 103 performs filtering in the spatial direction on the moving image representing the effective atomic number Z and the moving image representing the surface density D. For example, assume that $\beta_D$ represents the filter coefficient in the spatial direction for the surface density, $\beta_Z$ represents the filter coefficient in the spatial direction for the effective atomic number, D[x, y, t] represents the surface density at a coordinate (x, y) in the t-th frame, and Z[x, y, t] represents the effective atomic number at the coordinate (x, y) in the t-th frame. Also, D'[x, y, t] represents the surface density at the coordinate (x, y) in the t-th frame after application of a spatial filter, and Z'[x, y, t] represents the effective atomic number at the coordinate (x, y) in the t-th frame after application of the spatial filter. The control apparatus 103 performs filtering in the spatial direction by determining filter coefficients of the filtering using the equations shown below. Namely, the filtering unit of the control apparatus 103 performs filtering in the spatial direction on the first signal component and the second signal component that are obtained by emitting radiation at a plurality of levels of energy toward the object. Thereafter, the generation unit of the control apparatus 103 generates a moving image based on the first signal component and the second signal component subjected to the filtering.

$$D'[x,y,t]=(1-\beta_D)D[x,y,t]+(D[x-1,y,t]+D[x+1,y,t]+D[x,y-1,t]+D[x,y+1,t])\beta_D/4$$

$$Z'[x,y,t]=(1-\beta_Z)D[x,y,t]+(Z[x-1,y,t]+Z[x+1,y,t]+Z[x,y-1,t]+Z[x,y+1,t])\beta_Z/4$$

$$\beta_D[x,y,t]=0(|D[x,y,t]-D[x,y,t-1]|\leq T)$$

$$\beta_D[x,y,t]=\beta_D(|D[x,y,t]-D[x,y,t-1]|>T)$$

$$\beta_Z[x,y,t]=0(|D[x,y,t]-D[x,y,t-1]|\leq T)$$

$$\beta_Z[x,y,t]=\beta_Z(|D[x,y,t]-D[x,y,t-1]|>T) \quad (9)$$

According to these equations, the control apparatus 103 determines the filter coefficient $\beta_Z[t]$ for the moving image representing the effective atomic number Z based on a change in the image of the object 111 in the time direction in the moving image representing the surface density D. Furthermore, the control apparatus 103 determines the filter coefficient $\beta_D[t]$ for the moving image representing the surface density D based on a change in the image of the object 111 in the time direction in the moving image representing the surface density D. Alternatively, the control apparatus 103 may also determine the filter coefficient $\beta_Z[t]$ for the moving image representing the effective atomic number Z based on a change in the image of the object 111 in the spatial direction in the moving image representing the surface density D. Furthermore, the control apparatus 103 may also determine the filter coefficient $\beta_D[t]$ for the moving image representing the surface density D based on a change in the image of the object 111 in the spatial direction in the moving image representing the surface density D.

Next, a case will be described in which the control apparatus 103 performs both filtering in the time direction and filtering in the spatial direction on the moving image representing the effective atomic number Z and the moving image representing the surface density D. If the object 111 has moved for example, the control apparatus 103 reduces noise by increasing the coefficient of a filter in the spatial direction without increasing the coefficient of a recursive filter. Specifically, the control apparatus 103 performs filtering by determining filter coefficients of filtering in the spatial direction using the following equations to which definitions about the above-described equations apply.

$$D'[x,y,t]=(1-\beta_D)\{(1-\beta_D)D[x,y,t]+(D|[x-1,y,t]+D[x+1,y,t]+D[x,y-1,t]+D[x,y+1,t])\beta_D/4\}+\alpha_DD'[x,y,t-1]$$

$$Z'[x,y,t]=(1-\beta_Z)\{(1-\beta_Z)Z[x,y,t]+(Z|[x-1,y,t]+Z[x+1,y,t]+Z[x,y-1,t]+Z[x,y+1,t])\beta_Z/4\}+\alpha_ZD'[x,y,t-1]$$

$$\alpha_D[x,y,t]=\alpha_D$$

$$\beta_D[x,y,t]=0(|D[x,y,t]-D[x,y,t-1]|\leq T)$$

$$\alpha_D[x,y,t]=0$$

$$\beta_D[x,y,t]=\beta_D(|D[x,y,t]-D[x,y,t-1]|>T)$$

$$\alpha_Z[x,y,t]=\alpha_Z$$

$$\beta_Z[x,y,t]=0(|D[x,y,t]-D[x,y,t-1]|\leq T)$$

$$\alpha_Z[x,y,t]=0$$

$$\beta_Z[x,y,t]=\beta_Z(|D[x,y,t]-D[x,y,t-1]|>T) \quad (10)$$

According to these equations, the control apparatus 103 determines the filter coefficients $\alpha_Z[t]$ and $\beta_Z[t]$ for the moving image representing the effective atomic number Z based on a change in the image of the object 111 in the time direction in the moving image representing the surface density D. Furthermore, the control apparatus 103 determines the filter coefficients $\alpha_D[t]$ and $\beta_D[t]$ for the moving image representing the surface density D based on a change in the image of the object 111 in the time direction in the moving image representing the surface density D. Alternatively, the control apparatus 103 may also determine the filter coefficients $\alpha_Z[t]$ and $\beta_Z[t]$ for the moving image representing the effective atomic number Z based on a change in the image of the object 111 in the spatial direction in the moving image representing the surface density D. Furthermore, the control apparatus 103 may also determine the filter coefficients $\alpha_D[t]$ and $\beta_D[t]$ for the moving image representing the surface density D based on a change in the image of the object 111 in the spatial direction in the moving image representing the surface density D.

Note that the control apparatus 103 generates an output moving image using the moving image representing the surface density D and the moving image representing the effective atomic number Z, but the image L at the attenuation ratio of low energy or the image H at the attenuation ratio of high energy may also be used instead of the surface density D to reduce noise. Alternatively, an average value of the image L at the attenuation ratio of low energy and the image H at the attenuation ratio of high energy may also be used. Alternatively, a logarithm of the image L at the attenuation ratio of low energy or a logarithm of the image H at the attenuation ratio of high energy may also be used. In this example, the above-described first signal component represents a value (the attenuation ratio itself, an average value, or a logarithm) based on the attenuation ratio at a level of energy, and the above-described second signal component represents the effective atomic number.

Second Embodiment

A radiation imaging system according to a second embodiment will be described. The configuration (FIGS. 1 and 2) of the radiation imaging system is the same as that in the first embodiment. The operations (FIG. 3) performed by the control apparatus 103 to acquire a plurality of input moving images from the radiation imaging apparatus 104 and the operations (FIG. 4) for computing the image L at the attenuation ratio of low energy and the image H at the attenuation ratio of high energy are also the same as those in the first embodiment.

Figure 8:
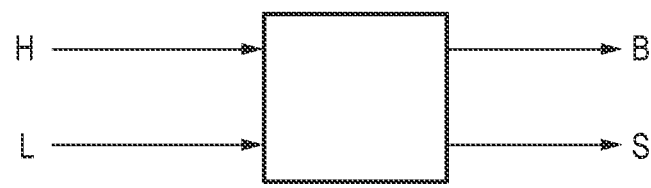
FIG. 8 is a diagram showing some operations of a control apparatus of a second embodiment.

A signal processing method performed in energy subtraction in the present embodiment will be described with reference to FIG. 8. The control apparatus 103 computes an image B that represents the thickness of a bone and an image S that represents the thickness of a soft tissue from the image L and the image H obtained through the processing shown in FIG. 4. The image L and the image H are based on the plurality of input moving images that the control apparatus 103 acquired from the radiation imaging apparatus 104, and accordingly the control apparatus 103 generates the image B representing the thickness of the bone and the image S representing the thickness of the soft tissue using the plurality of input moving images.

Assume that E represents energy of radiation photons, N(E) represents the photon number at the energy E, B represents the thickness of the bone, and S represents the thickness of the soft tissue. Also, $\mu_B(E)$ represents the linear attenuation coefficient of the bone at the energy E, $\mu_S(E)$ represents the linear attenuation coefficient of the soft tissue at the energy E, and $I/I_0$ represents the attenuation ratio. At this time, the following equation holds.

$$I/I_0 = \frac{\int_0^\infty N(E)\exp\{-\mu_B(E)B - \mu_S(E)S\}EdE}{\int_0^\infty N(E)EdE} \quad (11)$$

The photon number N(E) at the energy E is the spectrum of radiation. The spectrum of radiation is obtained through simulation or actual measurement. Also, the linear attenuation coefficient $\mu_B(E)$ of the bone at the energy E and the linear attenuation coefficient $\mu_S(E)$ of the soft tissue at the energy E are obtained from a database of NIST, for example. Namely, the attenuation ratio $I/I_0$ at a given thickness B of the bone, a given thickness S of the soft tissue, and a given spectrum N(E) of radiation can be calculated.

When $N_L(E)$ represents the spectrum of radiation of the rise period and the fall period and $N_H(E)$ represents the spectrum of radiation of the stable period, the following two equations hold.

$$L = \frac{\int_0^\infty N_L(E)\exp\{-\mu_B(E)B - \mu_S(E)S\}EdE}{\int_0^\infty N_L(E)EdE} \quad (12)$$

$$H = \frac{\int_0^\infty N_H(E)\exp\{-\mu_B(E)B - \mu_S(E)S\}EdE}{\int_0^\infty N_H(E)EdE}$$

Equations (12) are nonlinear simultaneous equations. By solving the simultaneous equations using the Newton-Raphson method, for example, the control apparatus 103 can compute the image representing the thickness B of the bone and the image representing the thickness S of the soft tissue from the image L at the attenuation ratio of low energy and the image H at the attenuation ratio of high energy.

Although the control apparatus 103 computes the image representing the thickness B of the bone and the image representing the thickness S of the soft tissue in the present embodiment, generally, the control apparatus 103 may compute an image that represents the thickness of a substance and an image that represents the thickness of another substance. For example, the control apparatus 103 may compute an image representing the thickness I of a contrast medium and an image representing the thickness S of the soft tissue.

Figure 9:
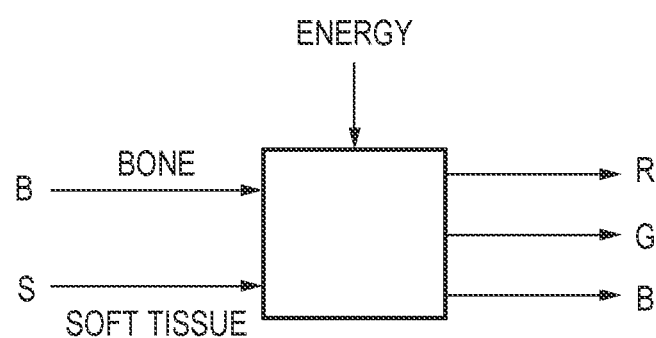
FIG. 9 is a diagram showing some operations of the control apparatus of the second embodiment.

An image processing method performed in energy subtraction processing in the present embodiment will be described with reference to FIG. 9. In image processing performed in the present embodiment, the control apparatus 103 determines values of two parameters that constitute a frame based on the image representing the thickness B of the bone and the image representing the thickness S of the soft tissue, and uses a prescribed value as the value of one parameter that constitutes the frame. As described above, the image representing the thickness B of the bone and the image representing the thickness S of the soft tissue are generated based on frames of the plurality of input moving images. Accordingly, the control apparatus 103 determines values of the two parameters based on the frames of the plurality of input moving images obtained by emitting radiation at a plurality of levels of energy toward the same object 111. The control apparatus 103 generates at least some frames of an output moving image using values of these three parameters.

In the present embodiment, the output moving image is a monochrome moving image, and the parameters determined based on the frames of the plurality of input moving images are the thickness B of the bone and the thickness S of the soft tissue. Each frame of the output moving image is a virtual monochromatic radiation image. For example, when $E_V$ represents energy of virtual monochromatic radiation, a virtual monochromatic radiation image V is obtained using the following equation. A monochrome frame is generated by setting the value of V for each of R, G, and B of the frame.

$$V = \exp\{-\mu_B(E_V)B - \mu_S(E_V)S\} \quad (13)$$

Next, filtering performed in the present embodiment will be described with reference to FIG. 10. In order to reduce noise of a virtual monochromatic radiation image, the control apparatus 103 performs filtering on a moving image representing the thickness B of the bone and a moving image representing the thickness S of the soft tissue. These moving images could be called two moving images obtained by emitting radiation at a plurality of levels of energy toward the same object 111. The control apparatus 103 generates an output moving image based on these moving images. The filtering performed by the control apparatus 103 may include filtering in the time direction, filtering in the spatial direction, or both of these. The control apparatus 103 generates the above-described output moving image based on the two moving images subjected to the filtering. In this example as well, the filtering unit of the control apparatus 103 performs filtering on a first signal component and a second signal component that are obtained by emitting radiation at a plurality of levels of energy toward the object. The first signal component represents the thickness of a first substance and the second signal component represents the thickness of a second substance.

A case will be described in which the control apparatus 103 performs filtering in the time direction on the moving image representing the thickness B of the bone and the moving image representing the thickness S of the soft tissue. Similarly to the first embodiment, filtering in the spatial direction may also be performed on these moving images, or both filtering in the time direction and filtering in the spatial direction may also be performed on these moving images. Processing that is performed using a recursive filter will be described as one example of filtering in the time direction. Assume that B[t] represents the thickness of the bone in the t-th frame, B'[t−1] represents the thickness of the bone in the t−1-th frame after application of the recursive filter, and $\alpha_B$ represents the coefficient of the recursive filter for the thickness of the bone. The control apparatus 103 calculates the thickness B'[t] of the bone in the t-th frame after application of the recursive filter, using the following equation.

$$B'[t] = \alpha_B * B'[t-1] + (1-\alpha_B) * B[t] \quad (14)$$

Likewise, assume that S[t] represents the thickness of the soft tissue in the t-th frame, S'[t−1] represents the thickness of the soft tissue in the t−1-th frame after application of the recursive filter, and as represents the coefficient of the recursive filter for the thickness of the soft tissue. The control apparatus 103 calculates the thickness S'[t] of the soft tissue in the t-th frame after application of the recursive filter, using the following equation.

$$S'[t]=\alpha_S*S'[t-1]+(1-\alpha_S)*S[t] \quad (15)$$

The coefficients $\alpha_B$ and $\alpha_S$ of the recursive filters are real numbers between 0 and 1. As a filter coefficient is increased, averaging of pixel values is performed going further back to the past, and accordingly noise is reduced. However, if the filter coefficient is too large, image lag occurs in a portion in which the object has moved.

In the case of an object of some type, the moving image representing the thickness B of the bone shows a smaller change in the time direction than the moving image representing the thickness S of the soft tissue shows. Therefore, if the coefficient $\alpha_B$ of the recursive filter for the thickness B of the bone is made larger than the coefficient $\alpha_S$ of the recursive filter for the thickness S of the soft tissue, image lag can be suppressed while noise of the virtual monochromatic radiation image is reduced. As a result, visibility of the moving image can be improved. In the case of an object of another type, visibility of the moving image can be improved by making the coefficient $\alpha_B$ B of the recursive filter for the thickness B of the bone smaller than the coefficient $\alpha_S$ of the recursive filter for the thickness S of the soft tissue. As described above, visibility of the moving image can be improved by individually setting filter coefficients such that the filter coefficient of filtering performed on the moving image representing the thickness B of the bone differs from the filter coefficient of filtering performed on the moving image representing the thickness S of the soft tissue.

Similarly to the first embodiment, in the present embodiment as well, the control apparatus 103 may also determine the filter coefficient in the time direction or the spatial direction for the moving image representing the thickness B of the bone based on a change in the image of the object 111 in the time direction or the spatial direction in the moving image representing the thickness S of the soft tissue. The control apparatus 103 may also determine the filter coefficient in the time direction or the spatial direction for the moving image representing the thickness S of the soft tissue based on a change in the image of the object 111 in the time direction or the spatial direction in the moving image representing the thickness S of the soft tissue.

In the present embodiment, the control apparatus 103 performs filtering on the moving image representing the thickness B of the bone and the moving image representing the thickness S of the soft tissue. Generally, the control apparatus 103 may perform filtering on a moving image representing the thickness of a substance and a moving image representing the thickness of another substance, and generate an output moving image based on the moving images subjected to the filtering. For example, the control apparatus 103 may perform filtering on a moving image representing the thickness I of a contrast medium and a moving image representing the thickness S of the soft tissue.

In the above-described example, the control apparatus 103 generates a virtual monochromatic radiation image using the thickness B of the bone and the thickness S of the soft tissue. Alternatively, the control apparatus 103 may also calculate the effective atomic number Z and the surface density D as is the case with the first embodiment, and generate a virtual monochromatic radiation image using the effective atomic number Z and the surface density D. In this case, the control apparatus 103 performs filtering on a moving image representing the effective atomic number Z and a moving image representing the surface density D and generates an output moving image based on the moving images subjected to the filtering. Alternatively, the control apparatus 103 may also generate a composite radiation image by compositing a plurality of virtual monochromatic radiation images generated using a plurality of levels of energy $E_V$. A composite radiation image is an image that is to be obtained if radiation of a given spectrum is emitted.

Variations

In the first embodiment and the second embodiment, the radiation imaging apparatus 104 is an indirect radiation sensor using a scintillator. Alternatively, the radiation imaging apparatus 104 may also be a direct radiation sensor using a direct conversion material such as CdTe, for example.

The radiation generating apparatus 101 utilizes a passive change in the tube voltage. Alternatively, the radiation generating apparatus 101 may also actively change the tube voltage. A configuration is also possible in which energy of radiation emitted toward the radiation imaging apparatus 104 is varied by temporally switching a filter of the radiation generating apparatus 101, for example.

In the above-described examples, energy subtraction is performed by varying energy of radiation emitted toward the radiation imaging apparatus 104. Alternatively, a method may also be employed in which two sensors are layered so that the spectrum of radiation changes between radiation detected by a front sensor and radiation detected by a rear sensor, for example. Alternatively, a plurality of images that differ from each other in energy may also be acquired using a photon counting sensor that counts the number of radiation quanta for each level of energy.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

With the above-described embodiments, the quality of an image generated using radiation at a plurality of levels of energy is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus, comprising:
   a filtering unit configured to perform filtering in a time direction on a first signal component and a second signal component that are obtained using energy images of an object, wherein the energy images are obtained as images of a plurality of levels of energy; and
   a processor and memory configured to generate a moving image based on the first signal component and the second signal component on which the filtering is performed, wherein
   a filter coefficient of the filtering performed on the first signal component and a filter coefficient of the filtering performed on the second signal component differ from each other.

2. The image processing apparatus according to claim 1, wherein the processor and memory are configured to determine the filter coefficient for the second signal component based on a change in the first signal component in a time direction.

3. The image processing apparatus according to claim 2, wherein the processor and memory are configured to determine the filter coefficient for the first signal component based on a change in the first signal component in the time direction.

4. The image processing apparatus according to claim 1, wherein the processor and memory are configured to determine the filter coefficient for the second signal component based on a change in the first signal component in a spatial direction.

5. The image processing apparatus according to claim 4, wherein the processor and memory are configured to determine the filter coefficient for the first signal component based on a change in the first signal component in the spatial direction.

6. The image processing apparatus according to claim 1, wherein the first signal component represents a surface density, and the second signal component represents an effective atomic number.

7. The image processing apparatus according to claim 1, wherein the first signal component represents a value that is based on an attenuation ratio at a level of energy, and
   the second signal component represents an effective atomic number.

8. The image processing apparatus according to claim 1, wherein the first signal component represents a thickness of a first substance, and
   the second signal component represents a thickness of a second substance.

9. The image processing apparatus according to claim 1, which is configured to emit radiation at the plurality of levels of energy in a single emission of radiation.

10. The image processing apparatus according to claim 1, wherein the filtering unit is configured to perform filtering in a time direction and in a spatial direction on the first signal component and the second signal component.

11. A non-transitory storage medium storing a program for causing a computer to function as the image processing apparatus according to claim 1.

12. A non-transitory storage medium storing a program for causing a computer to function as the image processing apparatus according to claim 10.

13. An image processing method, comprising the steps of:
   performing filtering in a time direction on a first signal component and a second signal component that are obtained using energy images of an object, wherein the energy images are obtained as images of a plurality of levels of energy; and
   generating a moving image based on the first signal component and the second signal component on which the filtering is performed, wherein
   a filter coefficient of the filtering performed on the first signal component and a filter coefficient of the filtering performed on the second signal component differ from each other.

14. A non-transitory storage medium storing a program for causing a computer to function as the image processing method according to claim 13.

* * * * *